(12) United States Patent
Shepard et al.

(10) Patent No.: US 11,112,360 B2
(45) Date of Patent: Sep. 7, 2021

(54) SYSTEM INCLUDING OPTICALLY-POWERED SENSING INTEGRATED CIRCUIT(S) WITH OPTICAL INFORMATION TRANSFER

(71) Applicant: THE TRUSTEES OF COLUMBIA UNIVERSITY IN THE CITY OF NEW YORK, New York, NY (US)

(72) Inventors: Kenneth Shepard, Ossining, NY (US); Girish Ramakrishnan, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 209 days.

(21) Appl. No.: 16/041,373

(22) Filed: Jul. 20, 2018

(65) Prior Publication Data
US 2019/0060663 A1    Feb. 28, 2019

Related U.S. Application Data

(63) Continuation of application No. PCT/US2017/014569, filed on Jan. 23, 2017.
(Continued)

(51) Int. Cl.
*A61N 5/06*        (2006.01)
*G01N 21/64*       (2006.01)
(Continued)

(52) U.S. Cl.
CPC ....... *G01N 21/6428* (2013.01); *A61B 5/0031* (2013.01); *G02F 1/025* (2013.01);
(Continued)

(58) Field of Classification Search
CPC .............. G01N 21/6428; A61B 5/0031; A61B 2560/0214; G02F 1/025; G02F 2001/0157; H01L 31/02327
See application file for complete search history.

(56) References Cited

U.S. PATENT DOCUMENTS

| 5,423,334 A | 6/1995 | Jordan |
| 6,447,448 B1 | 9/2002 | Ishikawa et al. |
| (Continued) | | |

FOREIGN PATENT DOCUMENTS

| CN | 205306997 U | 6/2016 |
| WO | WO 2014/126927 A1 | 8/2014 |

OTHER PUBLICATIONS

U.S. Appl. No. 15/911,973 (US 2018/0193000), filed Mar. 5, 2018 (Jul. 12, 2018).
(Continued)

*Primary Examiner* — Ermias T Woldegeorgis
(74) *Attorney, Agent, or Firm* — Hunton Andrews Kurth LLP

(57) ABSTRACT

Systems and methods for performing non-destructive sensing of a cell or tissue, in vivo or in culture, are provided. The disclosed systems and methods include fabricating and powering one or more implantable integrated circuit (IC) chips that include a network of Photovoltaic (PV) cells for energy harvesting from an optical energy source, an optical modulator integrating Quantum Dot capacitors (QD-caps) for optical data transfer using fluorescence modulation, and sensing circuitry. The IC chip disclosed herein can measure a thickness of around 10 µm, allowing injection into small cells and diffusion through tissue, it is powered and imaged under a microscope and communicates using fluorescence modulation imaged under a microscope.

16 Claims, 12 Drawing Sheets

Related U.S. Application Data

(60) Provisional application No. 62/281,566, filed on Jan. 21, 2016.

(51) Int. Cl.
| | |
|---|---|
| *A61B 5/00* | (2006.01) |
| *G02F 1/025* | (2006.01) |
| *H01L 31/0232* | (2014.01) |
| *G02F 1/015* | (2006.01) |

(52) U.S. Cl.
CPC .......... *H01L 31/02327* (2013.01); *A61B 2560/0214* (2013.01); *G02F 1/0157* (2021.01)

(56) References Cited

U.S. PATENT DOCUMENTS

| | | | |
|---|---|---|---|
| 6,539,253 | B2 | 3/2003 | Thompson et al. |
| 7,127,286 | B2 | 10/2006 | Mech et al. |
| 7,237,712 | B2 | 7/2007 | Derocco et al. |
| 7,904,160 | B2 | 3/2011 | Brodnick et al. |
| 8,108,048 | B2 | 1/2012 | Masoud |
| 8,183,745 | B2 | 5/2012 | Trolier-Mckinstry et al. |
| 8,292,834 | B2 | 10/2012 | El-bialy et al. |
| 8,591,419 | B2 | 11/2013 | Tyler |
| 8,764,677 | B2 | 7/2014 | Toumazou et al. |
| 8,824,161 | B2 | 9/2014 | Askarinya et al. |
| 9,079,137 | B2 | 7/2015 | Sim et al. |
| 2005/0027175 | A1 | 2/2005 | Yang |
| 2008/0085120 | A1 | 4/2008 | Xie et al. |
| 2008/0154101 | A1 | 6/2008 | Jain et al. |
| 2009/0238511 | A1 | 9/2009 | Quitoriano et al. |
| 2010/0105075 | A1 | 4/2010 | Harjes et al. |
| 2011/0009734 | A1 | 1/2011 | Foley et al. |
| 2011/0178578 | A1 | 7/2011 | Porat et al. |
| 2011/0237953 | A1 | 9/2011 | Olsson et al. |
| 2012/0041310 | A1 | 2/2012 | Towe |
| 2013/0043768 | A1 | 2/2013 | Cochran et al. |
| 2013/0187185 | A1 | 7/2013 | Deshazer et al. |
| 2013/0328416 | A1* | 12/2013 | Whitworth ............... F03G 5/06 307/149 |
| 2014/0058292 | A1 | 2/2014 | Alford et al. |
| 2014/0176066 | A1 | 6/2014 | Dronov et al. |
| 2014/0219062 | A1 | 8/2014 | Rothberg et al. |
| 2014/0309503 | A1 | 10/2014 | Arneson et al. |
| 2015/0008792 | A1 | 1/2015 | Gong et al. |
| 2015/0032002 | A1 | 1/2015 | Rothberg et al. |
| 2015/0112233 | A1 | 4/2015 | Towe et al. |
| 2016/0157717 | A1 | 6/2016 | Gaster |
| 2016/0207760 | A1 | 7/2016 | Rothberg et al. |
| 2016/0303402 | A1 | 10/2016 | Tyler |

OTHER PUBLICATIONS

Akin et al., "A Wireless Implantable Multichannel Digital Neural Recording System for a Micromachined Sieve Electrode," IEEE Journal of Solid-State Circuits, 33(1):109-118 (1998).

Cilingiroglu et al., "On-Chip Photovoltaic Energy Conversion in Bulk-CMOS for Indoor Applications," IEEE Trans. Circuits Syst.-I Regul. Pap., 61(8):2491-2504 (2014).

Denisov et al., "Ultrasonic vs Inductive Power Delivery for Miniature Biomedical Implants," 2010 International Conference on Body Sensor Networks, IEEE Computer Society, pp. 84-89 (Jun. 7-9, 2010).

Eggers et al., "Advanced Hybrid Integrated Low-Power Telemetric Pressure Monitoring System for Biomedical Applications," IEEE, pp. 329-334 (2000).

Figueiredo et al., "Optical modulation in a resonant tunneling relaxation oscillator," Applied Physics Letters, 74(9):1197-1199 (1999).

Fong et al., "Integrated Energy-Harvesting Photodiodes with Diffractive Storage Capacitance," IEEE Trans. Very Large Scale Integr. (VLSI) Syst., 21(3):486-497 (2013).

Ghosh et al., "A Circuit for Energy Harvesting Using On-Chip Solar Cells," IEEE Trans. Power Electron., 29(9):4658-4671 (2014).

Hannan et al., "Energy harvesting for the implantable biomedical devices: issues and challenges," Biomed. Eng. Online 13:79 (2014).

Harrison et al., "A Low-Power Integrated Circuit for a Wireless 100-Electrode Neural Recording System," IEEE Journal of Solid-State Circuits, 42(1):123-133 (2007).

Harrison et al., "A Low-Power, Low-Noise CMOS Amplifier for Neural Recording Applications," IEEE Journal of Solid-State Circuits, 38(6):958-965 (2003).

Ho et al., "Wireless power transfer to deep-tissue microimplants," PNAS 111(22):7974-7979 (2014).

International Search Report and Written Opinion dated Mar. 13, 2018 in International Application No. PCT/US17/68528.

International Search Report dated Jan. 5, 2017 in International Application No. PCT/US16/50165.

International Search Report dated Sep. 13, 2017 in International Application No. PCT/US17/14569.

Jackson et al., "Flexible-CMOS and biocompatible piezoelectric AlN material for MEMS applications," Smart Materials and Structures 22:115033 (2013).

Kim et al., "CMOS Ultrasound Transceiver Chip for High-Resolution Ultrasonic Imaging Systems," IEEE Transactions on Biomedical Circuits and Systems 3(5):293-303 (2009).

Kim et al., "Flexible and Stretchable Electronics for Biointegrated Devices," Annual Review of Biomedical Engineering 14:113-128 (2012).

Kocer et al., "A New Transponder Architecture with On-Chip ADC for Long-Range Telemetry Applications," IEEE Journal of Solid-State Circuits, 41(5):1142-1148 (2006).

Lin et al., "A sub-pW timer using gate leakage for ultra low-power sub-Hz monitoring systems," 2007 IEEE Custom Integrated Circuits Conference, pp. 397-400 (2007).

Lu et al., "Ultrasonic fingerprint sensor using a piezoelectric micromachined ultrasonic transducer array integrated with complementary metal oxide semiconductor electronics," Applied Physics Letters 106(26):263503 (2015).

Misri et al., "Microfabrication of bulk PZT transducers by dry film photolithography and micro powder blasting," Journal of Micromechanics and Microengineering 22:085017 (2012).

Pour et al., "Energy Harvesting Using Substrate Photodiodes," IEEE Trans. Circuits Syst.—II: Express Briefs, 61(7):501-505 (2014).

Samaun et al., "An IC Piezoresistive Pressure Sensor for Biomedical Instrumentation," IEEE Transactions on Biomedical Engineering, 20(2):101-109 (1973).

Schwiebert et al., "Research Challenges in Wireless Networks of Biomedical Sensors," ACM, pp. 151-165 (2001).

Shrivastava, Analysis and Design of A 3-stage Voltage Rectifier Multiplier and 2-stage Multi-Phase Voltage Doubler for an Energy Harvesting System. A Thesis. Texas Tech University, Aug. 2012.

Stieglitz et al., "Implantable Biomedical Microsystems for Neural Prostheses," IEEE Engineering in Medicine and Biology Magazine, 24(5):58-65 (2005).

Stieglitz et al., "Micromachined, Polyimide-Based Devices for Flexible Neural Interfaces," Biomedical Microdevices 2(4):283-294 (2000).

Sun et al., "Series resonant ZCS-PFM DC-DC converter with multistage rectified voltage multiplier and dual-mode PFM control scheme for medical-use high-voltage X-ray power generator," IEE Proceedings—Electric Power Applications, 147(6):527-534 (2000).

Tyler et al., "Remote Excitation of Neuronal Circuits Using Low-Intensity, Low-Frequency Ultrasound," PLoS ONE 3(10):e3511 (2008).

Wong et al., "A Very Low-Power CMOS Mixed-Signal IC for Implantable Pacemaker Applications," IEEE Journal of Solid-State Circuits, 39(12):2446-2456 (2004).

* cited by examiner

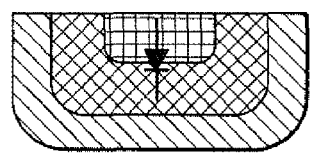
FIG. 8A
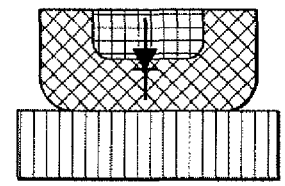
FIG. 8D
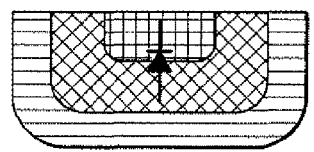
FIG. 8B
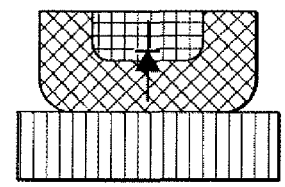
FIG. 8E
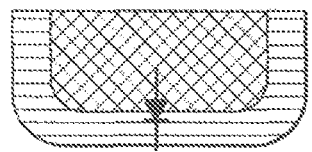
FIG. 8C
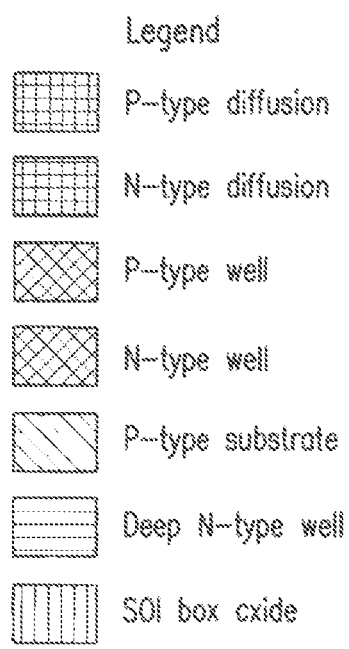

SYSTEM INCLUDING OPTICALLY-POWERED SENSING INTEGRATED CIRCUIT(S) WITH OPTICAL INFORMATION TRANSFER

CROSS REFERENCE TO RELATED APPLICATION

This application is a Continuation of International Patent Application No. PCT/US2017/014569, which was filed Jan. 23, 2017, which claims prioirity to U.S. Provisional Patent Application No. 62/281,566, entitled "Micron-Scale Active Complementary Metal-Oxide-Semiconductor (CMOS) Optical Tags," which was filed on Jan. 21, 2016, the entire contents of which are incorporated by reference herein.

STATEMENT REGARDING FEDERALLY FUNDED RESEARCH

This invention was made with government support under Grant No. N000141310375 awarded by the Office of Naval Research. The U.S. government has certain rights in this invention.

BACKGROUND

Implanted and injected integrated circuits can provide an array of functionalities in diverse fields such as sensing of biomedical signals, drug delivery in targeted tissues, cell stimulation and overall monitoring of signals. In these applications, the integrated circuit (IC) can be appropriately passivated and can operate as the entire implanted system. In designing such chips, characteristics including size, power delivery and communication can determine the efficacy and outcome of the desired application.

Specifically, the IC size can affect the area and manner in which it can be implanted and injected. For example, millimeter-scale chips can be often implanted at regions of interest only through surgery. Furthermore, at these scales, chips can be invasive to the living system in which they are embedded and can cause adverse effects to surrounding tissue. In addition, millimeter-scale chips, due to their large size, are not suitable for long-term sensing in the hosting tissue in order to obtain and measure characteristic signals related to intracellular or extracellular activity. Indeed, such chips are not capable of diffusing through tissue and perform their functions on more localized length scales.

Furthermore, power delivery to implanted chips can be performed wirelessly. Certain wireless power configurations can involve coupling to electromagnetic or mechanical waves. Electromagnetic coupling at long wavelengths, such as in the radio frequency spectrum, can be performed using millimeter-scale antennas or the like for efficient energy capture. However, introducing additional hardware can increase the scaling of the IC chip. Alternatively, near-field power transfer can be performed between an implanted IC chip. However, such configurations can require that the IC chip is proximate to an external transceiver. In addition, energy harvesting from ultrasound can also be performed in implantable chips. Ultrasound can have a lower wavelength, and thus can operate with smaller antennas, such as, for example, transducers. However, the scalability of ultrasound to a few micron- (μm-) scale chips can be difficult, for example when utilizing high ultrasound frequencies that can have difficulty penetrating tissue.

Accordingly, there is a need for miniaturized implantable IC chips that are efficiently powered and can interface with the host tissue in order to perform non-destructive sensing and imaging of a cell and/or a tissue sample.

SUMMARY

In a first aspect of the disclosed subject matter, systems for performing non-destructive sensing of one or more cells or tissue using integrated circuits (IC) such as complementary metal-oxide-semiconductors (CMOS) are provided. According to aspects of the present disclosure, the integrated circuit can include an energy harvestor e.g., energy harvesting circuitry that is capable of collecting light/energy from an optical source. Using the harvested energy, the integrated circuit can power the existing circuitry and also provide optical signals for transmission. For example, in some embodiments an energy harvestor can include one or more photovoltaic cells. The integration of energy harvesting circuitry directly on the chip helps to improve the scale of the integrated circuit and ensures near perpetual operation by using ambient energy sources.

In some embodiments, the integrated circuit can include a sensor e.g., sensing circuitry coupled to the energy harvestor to be powered by the collected energy and configured to measure one or more electrical or electrochemical signals associated with the one or more cells or tissues. Furthermore, the integrated circuit can include at least one optical modulator configured to transmit the one or more electrical or electrochemical signals as one or more optical signals. Specifically, the sensing circuitry and optical modulator can be coupled to the energy harvestor allowing them to be powered by the harvested energy and modulate the optical signal that is subsequently transmitted. In some embodiments, the optical modulator can be post-processed on the IC chip, thus providing for transmitting electrical signals as optical signals that can be captured by a variety of imaging tools including cameras mounted on epi-fluorescent microscopes.

The implantable IC chips can be fashioned with certain fabrication techniques to improve size by reducing thickness and can incorporate energy harvesting circuits.

In accordance with an exemplary embodiment, a method for performing non-destructive sensing of a cell or a tissue—in vivo, or in culture using an IC chip, is provided. Initially, the integrated circuit is implanted into the cell by, for example, injection of the integrated circuit to the desired tissue. The implanted IC chip can include an energy harvestor e.g., energy harvesting circuitry configured to collect light from an optical source such as a lamp and/or ambient light. Furthermore, the implanted IC chip can include sensing circuitry coupled to the energy harvestor so as to be powered by the collected light and configured to measure one or more electrical or electrochemical signals associated with the cell. In addition the IC chip can include at least one optical modulator configured to receive the one or more electrical signals and generate one or more optical signals.

In order to perform the sensing of the cell, the method can include receiving, by the integrated circuit, light transmitted by the optical source using the energy harvestor that is capable of powering the integrated circuit. In addition, modulating the one or more electrical signals with the transmitted light, by the optical modulator to generate the one or more optical signals. The method can further include transmitting the one or more optical signals, by the optical modulator. In some embodiments, the transmitted one or more optical signals can be subsequently detected by an image sensor that is configured to measure and display the one or more optical signals.

BRIEF DESCRIPTION OF THE DRAWINGS

FIGS. 8A-8E illustrate exemplary structures of energy harvesting circuitry of the disclosed integrated circuit in a CMOS process, in accordance with one or more embodiments.

DETAILED DESCRIPTION

Figure 1:
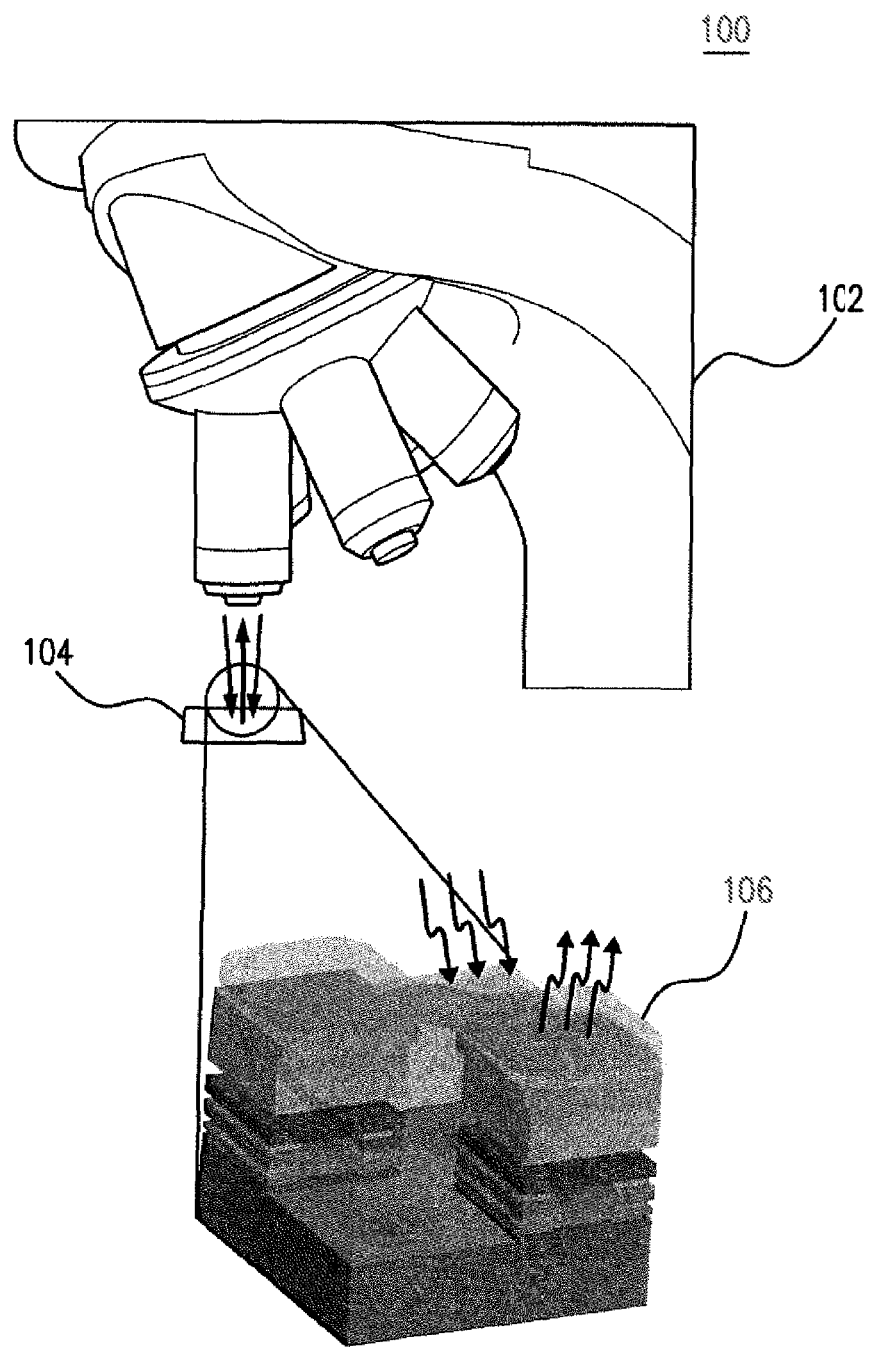
FIG. 1 illustrates an exemplary system for performing non-destructive sensing and imaging of a cell, in accordance with one or more embodiments.

Systems and methods for performing non-destructive sensing and imaging of a cell using integrated circuits (IC) such as complementary metal-oxide-semiconductors (CMOS) are provided. According to aspects of the present disclosure, the integrated circuit is implanted in the tissue of interest and can include an energy harvestor e.g., energy harvesting circuitry that is capable of collecting light from an optical source in order to power the integrated circuit. Visible light can provide advantages over certain conventional wireless power supply techniques for implanted IC chips, at least in part, because visible light has a wavelength ranging from 400 nm to 700 nm. Accordingly, the wavelength can be smaller than the size of a few-micron-scale chip, and thus interference or diffraction can be reduced or eliminated. In addition, light can directly transfer energy to silicon, which can have a bandgap of 1.12 eV, and thus the chip can be implemented without an explicit transducer. As a result, the size of the IC chip can be reduced.

In some embodiments, such energy harvesting circuitry can include one or more photovoltaic cells, a photovoltaic transducer or any other suitable energy harvesting circuitry. The integration of energy harvesting circuitry directly into the CMOS IC chip e.g., via front-end processing helps to improve the scale of the integrated circuit and ensures near perpetual operation by using ambient energy sources. These optically powered μm-scale chips with the integrated energy harvestor can be coupled with sensing electronics and logic functionalities in order to perform localized electrophysiological measurements, act as intracellular probes and can perform certain optically triggered stimulations.

In some embodiments, the implantable integrated circuit can include at least one optical modulator configured to transmit one or more electrical or electrochemical signals as one or more optical signals. Specifically, the optical modulator can be connected to the sensing electronics and energy harvestor so as to be powered by the harvested energy and modulate the optical signal that is subsequently transmitted. In some embodiments, modulating the optical signal can be achieved by modulating the intensity of the optical signal, the wavelength of the optical signal, both the intensity and wavelength or any other suitable combination. Specifically, the optical modulator can be post-processed on the IC chip, thus providing for transmitting electrical signals as optical signals that can be captured by a variety of imaging tools. In some embodiments, modulation of light can be accomplished by using various fluorescent materials post-processed on the IC chip, which can reduce the overall consumption of power and allow for prolonged operation of the IC chip.

In some embodiments, the implantable IC chips of the disclosed subject matter can be smaller than 10 μm in each dimension and can utilize visible light to power the IC chip and scaled CMOS technology to design electronics. Furthermore, in some embodiments, the implantable IC chips of the present disclosed subject matter can be smaller than 10 μm in each dimension. For example, the thickness of the IC chip can be reduced to approximately 10 μm through wafer/chip-thinning processes including, for example, back-side grinding, deep-reactive ion etching (DRIE), a 65 nm bulk process or any other suitable size reduction technique. In some embodiments, fully fabricated IC chips can be collected in de-ionized water and can be injected to a cell and/or tissue of interest.

In some embodiments, the physical circuit of the chip can include additional components including, a relaxation oscillator and a driver for driving the optical modulator. Furthermore, the power consumption can be reduced or minimized with a measured operating power of approximately 100 pW and measured oscillator frequency to modulate the electro-optic modulator of approximately 1.2 Hz. In some embodiments, changing the oscillation frequency, such as for example, by making modifications in the front-end silicon fabrication, or, for example, by modifying the electro-optic modulator across instances can result to different operational characteristics of the IC circuit relating to the tissue of interest.

It is to be understood that both the foregoing general description and the following detailed description are exemplary and are intended to provide further explanation of the disclosed subject matter.

The accompanying drawings, which are incorporated in and constitute part of this specification, are included to illustrate and provide a further understanding of the disclosed subject matter. Together with the description, the drawings serve to explain the principles of the disclosed subject matter.

FIG. 1 illustrates an exemplary system 100 for performing non-destructive sensing and imaging of a cell. The exemplary embodiment depicted in FIG. 1 shows the IC chip 106 implanted in a cell placed on a microscopic slide 104. In some embodiments, IC chip 106 can be placed in solution or can be introduced into cells, tissues (e.g., in vivo or in culture) or cell cultures by injection/microinjection, endocytosis, or any other suitable technique. For example, in some embodiments, the integrated circuit can be coated with a biocompatible material allowing the cell and/or tissue to accept the implantation. In some embodiments, the integrated circuit can be implanted in the tissue by use of a micropipette from a dispersion or solution in a compatible solvent such as deionized (DI) water. In some embodiments, IC chip 106 can be injected into any place of interest, such as, for example, individual cells and/or tissues, cell cultures, water or any other suitable area of interest. In some embodiments, IC chip can be fabricated to have dimensions of approximately 10 μm×10 μm×10 μm in order to fascilitate placement of the IC chip and reduce interference and/or diffraction from visible light. The cell implanted IC chip 106 can be observed, for imaging and measuring purposes, by placing microscopic slide 104 under microscope 102. In some embodiments, microscope 102 can be a laboratory epi-fluorescent microscope including, for example, CMOS and Charged-Coupled Device (CCD) cameras, a spectrometer, a light source or other suitable optical probe/sensor configured to detect optical signals.

Figure 2A:
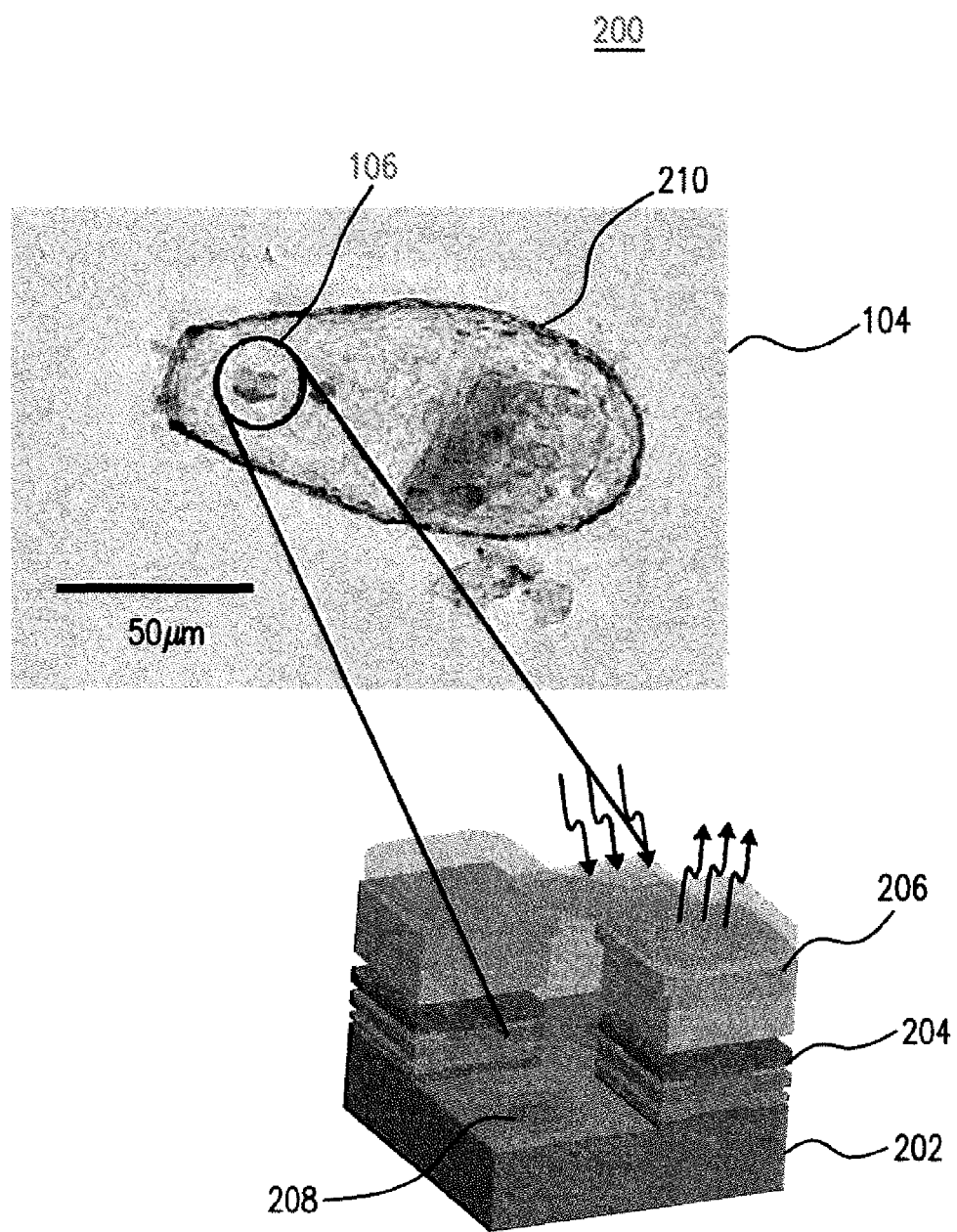
FIG. 2A illustrates an exemplary side perspective view of the disclosed integrated circuit, in accordance with one or more embodiments.

FIG. 2A, illustrates a large scale, top view of a microscopic slide 104 including cell 210 and an example implant IC chip 106. In addition, FIG. 2A shows a larger side perspective view of implanted IC chip 106. IC chip 106 includes various layered regions including backside substrate 202, frontside substrate 204, optical modulator 206 and energy harvesting circuitry 208. Specifically, in some embodiments, backside substrate 202 can be a carrier substrate including a p-type semiconductor substrate fabricated using CMOS bulk processes. Similarly, frontside substrate 204 can be any suitable silicon substrate mounted onto carrier backside substrate 202 and fabricated using CMOS bulk processes such as a 65 nm bulk process. For example, in some embodiments, the thickness of the IC chip can be reduced from 300 μm thick to approximately 10 μm through various wafer/chip-thinning processes including, for example, back-side grinding and deep-reactive ion etching (DRIE), removing the backside silicon by backside mechanical grinding, chemical mechanical polishing (CMP), physical or chemical etching, controlled spalling or any suitable combination of thinning processes. In some embodiments, the ultra-thin chip can be transferred to a flexible or rigid substrate, either before the thinning procedure, after the thinning procedure, or during the thinning process.

Optical modulator 206 can be post-processed on the CMOS IC chip such that it is over backside substrate 202 and frontside substrate 204. In some embodiments, optical modulator 206 can be fabricated using different techniques that are discussed below in reference to FIGS. 2B-4J. Energy harvesting circuitry 208 can be integrated directly into the CMOS IC front-end processing during fabrication of backside substrate 202. Such circuitry can provide techniques for converting light falling on it into usable electrical energy. For example, light can directly transfer energy to silicon, including backside substrate 202 and frontside substrate 204 which can have a bandgap of 1.12 eV, and thus the implant IC chip 106 can be implemented without additional hardware e.g., an explicit transducer, which can reduce its overall size. Energy harvesting circuitry 208 can be any suitable circuitry that can collect energy from natural and/or manufactured ambient energy sources such as lamps, sound, ambient light and others and will be further discussed below in reference to FIG. 2B.

Figure 2B:
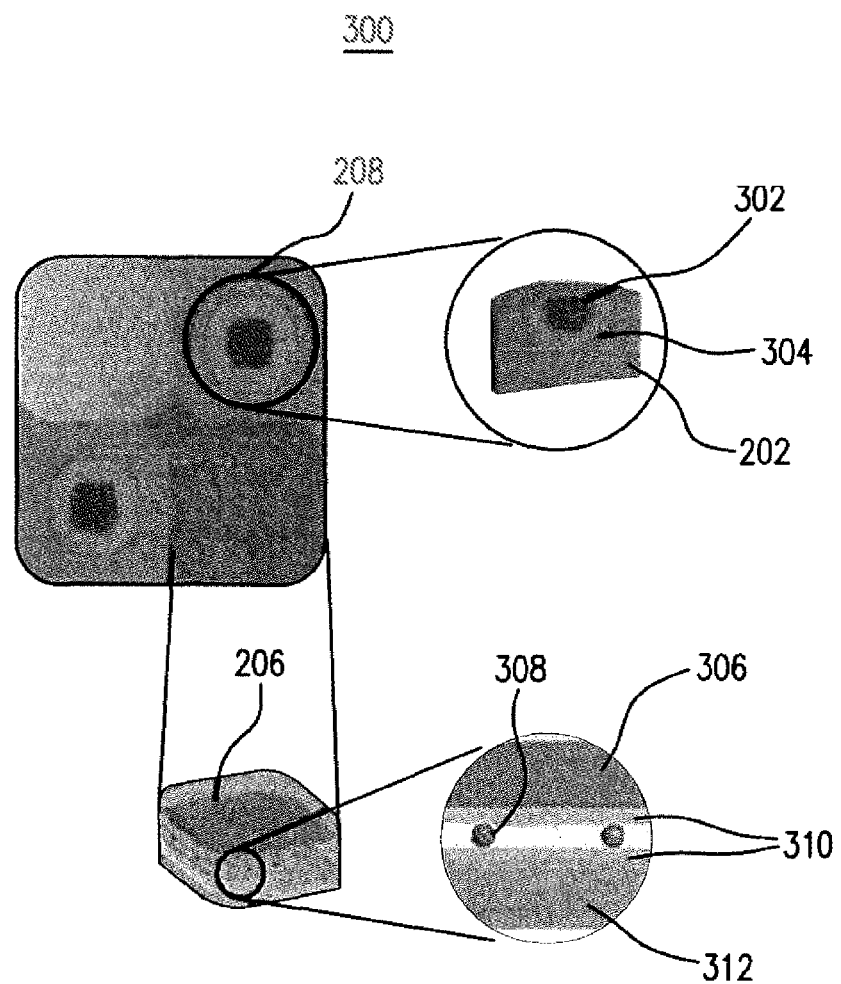
FIG. 2B illustrates an exemplary top view including cross-sectional views of the disclosed integrated circuit, in accordance with one or more embodiments.

FIG. 2B illustrates an exemplary top view including cross-sectional views of the implant integrated circuit 106 previously illustrated in FIG. 2A. Specifically, implant IC 106 includes optical modulator 206 and energy harvesting circuitry 208. Optical modulator 206 is post-processed on the chip and is capable of modulating and transmitting an optical signal detectable by optical probes/sensors, such as microscopes and cameras. In some embodiments, optical modulator 206 is an electro-optical modulator processed on the chip that can consume close to zero electrical power by using, for example, fluorescence material to emit optical signals. Specifically, in some embodiments, the IC chip 106 can be powered by light interacting with it and can transmit information by electrical modulation of an optical signal using quantum dot fluorescence.

For example, the optical modulator 206 can be fabricated using a dielectric stack of quantum dots 308 disposed between a dielectric material 310, such as hafnia, zirconia, alumina, silicon dioxide, or any other suitable thin film dielectric in order to form a quantum-dot capacitor (QDcap). In some embodiments, the dielectric 310 is chosen according to a low extinction coefficient and a high dielectric constant in order to increase or maximize the optical modulation. This can be achieved by modulating the fluorescence intensity or emission spectrum of quantum dots 308 using the Stark effect, modulating fluorescence quenching of quantum dots 308 on a 2-D material, such as for example, graphene, by modulating carrier sheet density of the 2-D material, modulating forward bias across μLEDs, or using MEMs digital micro-mirror devices to modulate direction of light reflectance off the surface of the chip or any other suitable modulation technique. In some embodiments, using the Stark effect to modulate fluorescence emission of quantum dots can provide upto 10% optical modulation depth at ~50 fW of power consumption and can allow easy scalability of fabrication process to die-level or wafer-level processing.

Furthermore, IC chip 106 includes top electrode 306 that can be implemented as a thin film transparent conductor to optically discern the fluorescence signal. In some embodiments, the top electrode 308 of the capacitor can be formed using indium tin oxide (ITO) and poly(3,4-ethylenedioxythiophene) polystyrene sulfonate (PEDOT:PSS) or any suitable thin film conductor. In some embodiments, ITO can be utilized at least in part to allow depositing of thin films of well-controlled thicknesses.

In addition, implant IC chip 106 includes energy harvesting circuitry 206 that collects light used for powering the integrated circuit. In some embodiments, energy harvesting circuitry 206 includes one or more photovoltaic cells that are fabricated using backside substrate 202 e.g., p-substrate, deep N-well substrate 304 and p-well substrate 302 as will be discussed in FIG. 8.

Figure 3A:
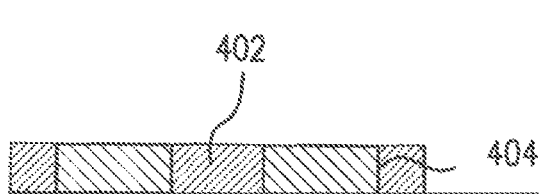
FIGS. 3A-3J illustrate an exemplary etching fabrication process for producing the optical modulator of the disclosed integrated circuit, in accordance with one or more embodiments.
Figure 3F:
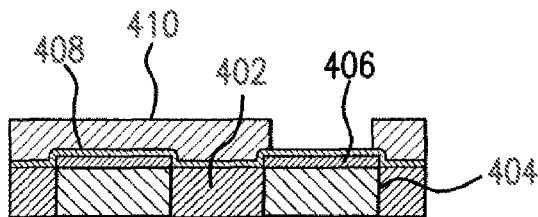
Figure 3B:
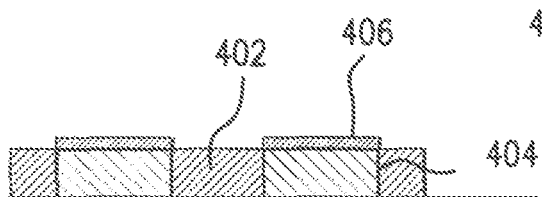

FIGS. 3A-3F illustrate an exemplary etching fabrication process for producing the optical modulator 206 integrated in IC chip 106. FIG. 3A shows bulk silicon chips after passivation removal and top metal layer exposed including a region of silicon CMOS substrate 402 and one or more regions 404 that includes a metal such as aluminum. FIG. 3B shows the deposition of one or more electrodes 406 over aluminum regions 404. In some embodiments, electrodes 406 are fabricated using gold or any other suitable material and can be lithographically defined and placed to form the electrical contacts on the modulator.

Figure 3G:
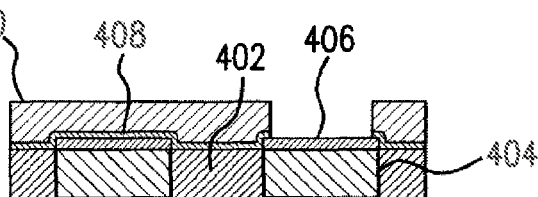
Figure 3C:
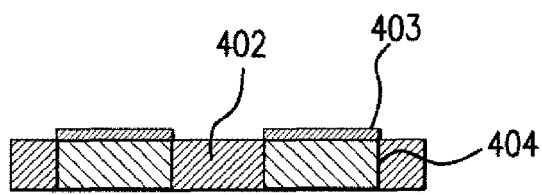
Figure 3H:
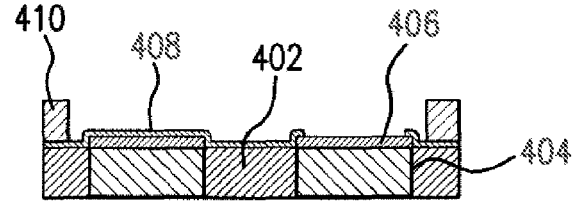
Figure 3D:
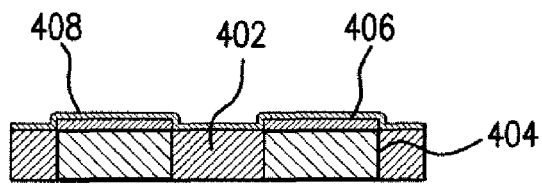
Figure 3I:
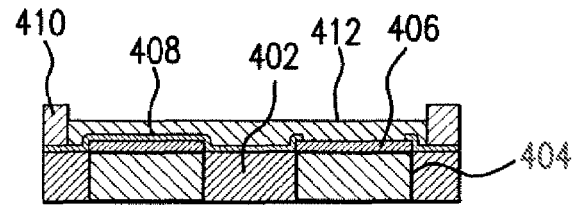
Figure 3E:
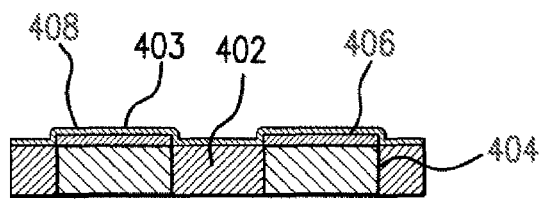

FIGS. 3C-3E show an example process for atomic layer deposition (ALD) of dielectric material 310 such as hafnia. For example, FIG. 3C shows the deposition of a first layer of hafnia 403 over substrate region 402 and aluminum regions 404 in order to form a hafnia-quantum dot-hafnia stack required for the quantum dot capacitor described in reference to FIG. 2B. Following the deposition of the first hafnia layer 403, FIG. 3D shows the deposition of quantum dot layer 408. In some embodiments, quantum dot layer 408 includes collodial quantum dots being spin coated on the chip. Subsequently, FIG. 3E shows the deposition of a second layer of hafnia 405.

In FIG. 3F, photoresist material 410 is applied to a portion of the chip. For example, an etch mask can be defined with an opening over one of the regions 404 to etch out the stack using a dry/wet etch strategy Specifically, deposition of the photoresist material 410 can be achieved by a photoresist (PR) spin coat and patterning etch mask in order to protect the deposition of the quantum dot layer 408 and ensure the efficiency of the optical modulator.

Figure 3J:
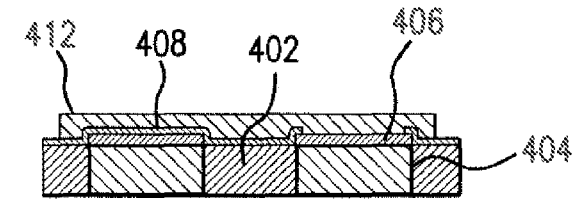

FIG. 3G shows the hafnia-QD stack etch through the photoresist mask 410. FIG. 3H shows the deposition mask for patterning of the top electrode 308 of the capacitor. The deposition of the top electrode 308 is shown in FIG. 3I. In some embodiments, the top electrode 308 can be formed using indium tin oxide (ITO) 412 and a new mask can be lithographically defined for the ITO 412, and the ITO can be deposited by sputtering or by electron beam deposition and can be patterned using a lift-off based strategy. FIG. 3J shows the photoresist material 410 removal and ITO 412 patterning by lift-off.

Figure 4A:
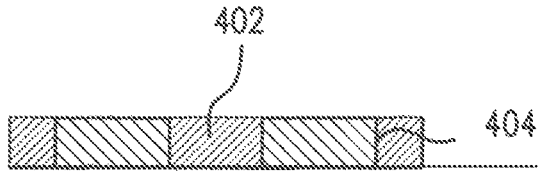
FIGS. 4A-4J illustrate an exemplary lift-off process for producing the optical modulator of the disclosed integrated circuit, in accordance with one or more embodiments.
Figure 4F:
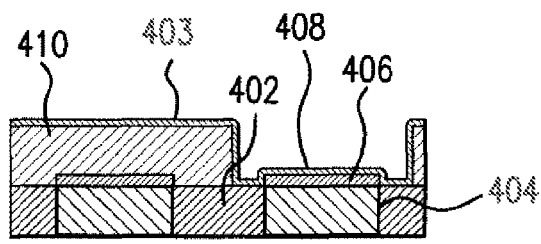
Figure 4B:
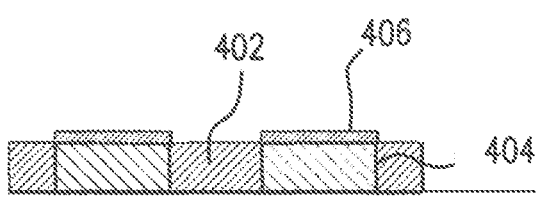
Figure 4G:
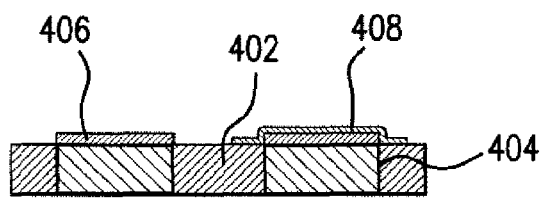
Figure 4C:
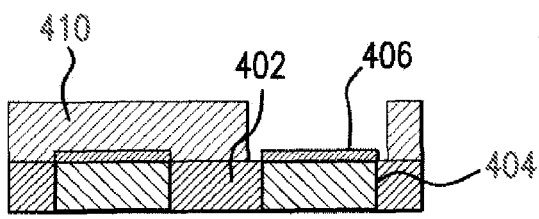

Additionally or alternatively, optical modulator 206 can also be fabricated by a lift-off fabrication process as shown in FIGS. 4A-4J. FIG. 4A shows bulk silicon chips after passivation removal and top metal layer exposed including a region of silicon CMOS substrate 402 and one or more regions 404 that includes a metal such as aluminum. FIG. 4B shows the deposition of one or more electrodes 406 over aluminum regions 404. In some embodiments, electrodes 406 are fabricated using gold or any other suitable material and can be lithographically defined and placed to form the electrical contacts on the modulator. In FIG. 4C, photoresist material 410 is applied to a portion of the chip. For example, a window can be lithographically defined over one of the regions 404 to define the hafnia-QD-hafnia stack. Specifically, deposition of the photoresist material 410 is achieved by a photoresist (PR) spin coat and patterning etch mask.

Figure 4H:
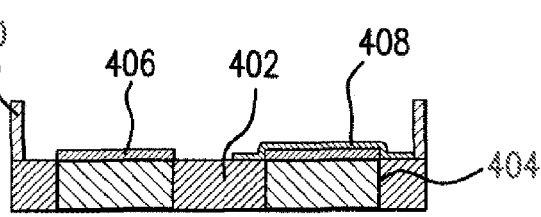
Figure 4D:
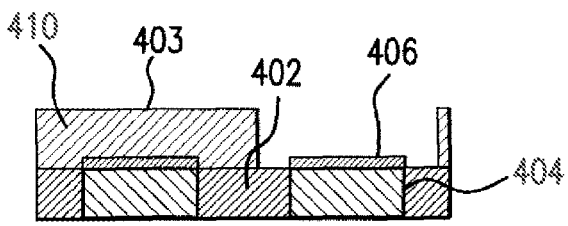
Figure 4I:
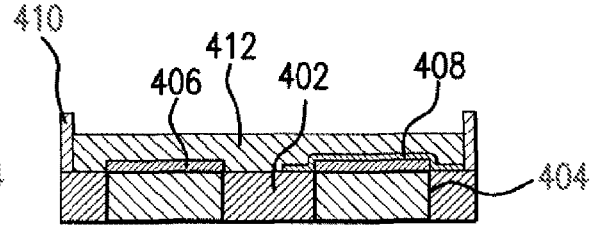
Figure 4E:
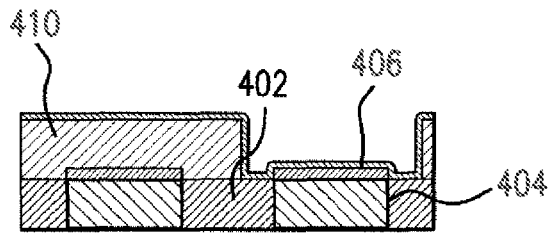
Figure 4J:
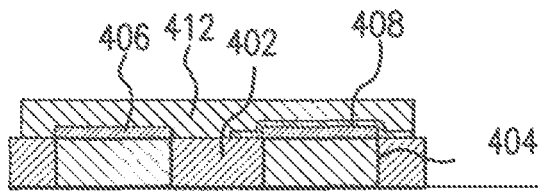

FIGS. 4D-4F show a process for atomic layer deposition (ALD) of dielectric material 312 such as hafnia. For example, FIG. 4D shows the deposition of a first layer of hafnia 403 over photoresist material 410, a portion of substrate region 402 and single aluminum region 404. Following the deposition of the first hafnia layer 403, FIG. 4E shows the deposition of quantum dot layer 408. In some embodiments, quantum dot layer 408 includes collodial quantum dots being spin coated on the chip. Subsequently, FIG. 4F shows the deposition of a second layer of hafnia 405. FIG. 4G shows the hafnia-quantum dot stack lift-off. FIG. 4H shows the deposition mask for patterning of the top electrode 308 of the capacitor. The deposition of the top electrode 308 is shown in FIG. 4I. In some embodiments, the top electrode 308 can be formed using indium tin oxide (ITO) 412 and a new mask can be lithographically defined for the ITO 412, and the ITO can be deposited by sputtering or by electron beam deposition and can be patterned using a lift-off based strategy. Lastly, FIG. 4J shows the photoresist material 410 removal and ITO 412 patterning by lift-off.

As discussed above in reference to FIG. 2B, the implant IC chip 106 with the integrated optical modulator 206 can be rendered thin in order to allow for the non-destructive implantation in the tissue of interest. In some embodiments, the thinning can be one of the last fabrication procedures, at least in part, because of the handling difficulties associated with thin dies. In some embodiments, the implant IC chip 106 can be thinned earlier into the process. Specifically, the thinning can include a variety of processes including mechanical grinding, CMP, physical etching, chemical etching or a combination of any suitable thinning process.

Figure 5A:
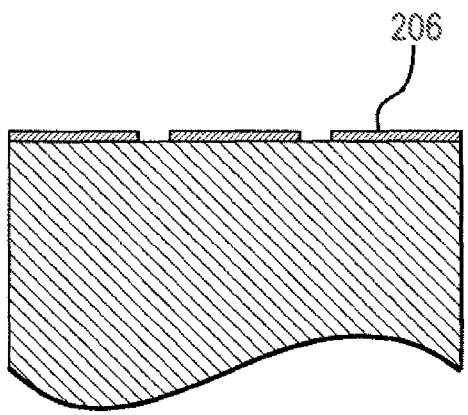
FIGS. 5A-5G illustrate an exemplary thinning process for producing the CMOS of the disclosed integrated circuit, in accordance with one or more embodiments.
Figure 5B:
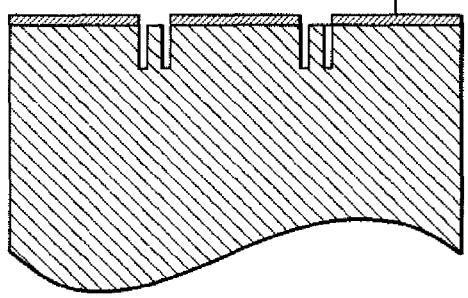

FIGS. 5A-5G illustrate an exemplary thinning process for producing one or more implant CMOS integrated circuits 106. Specifically, FIG. 5A shows bulk CMOS chip including the die backside substrate 202 after post-processing optical modulator 206. In some embodiments, anisotropic etching is performed in order to determine chip boundary demarcations that can be defined by forming vertical trenches 501 around the chip area, as shown in FIG. 5B. In some embodiments, anisotropic etching can be performed using a sequence of etch procedures, as the frontside of the CMOS chip can differ in material properties from the backside of the CMOS chip. Such process can fascilitate the chip release after fabrication.

Figure 5C:
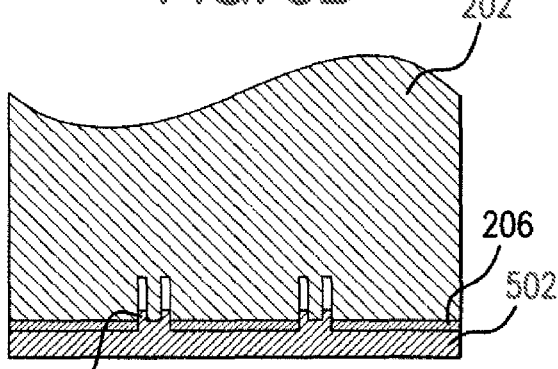
Figure 5D:
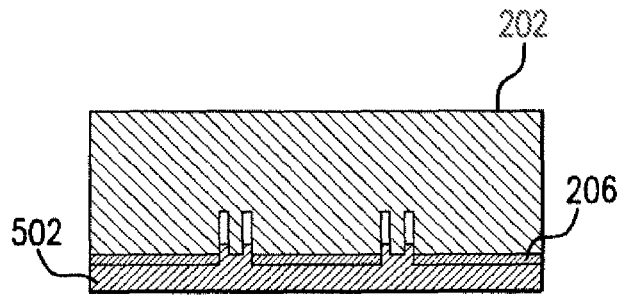

In FIG. 5C, the exemplary thinning process provides topside encapsulation that places biocompatible layer 504 and topside mounting CMOS substrate 502 onto carrier substrate 202. In some embodiments, biocompatible layer 504 can include parylene or any other suitable biocompatible material in order to allow for compatibility of implant IC chip 106 within the tissue of interest. Specifically, in some embodiments, the frontside substrate can be passivated by a conformal parylene coating which can be deposited in room temperature. The coating can render the chip biocompatible to inhibit or prevent it from being attacked by any reagents. In addition, FIG. 5D shows coarse chip-thinning using backside grinding in order to reduce the size and thickness of substrate 202.

Figure 5E:

FIG. 5E shows fine chip-thinning using deep reactive ion etching (DRIE) or any other suitable etching technique. For example, the backside etch can be performed by a sequence of mechanical grinding, mechanical smoothening and/or polishing and deep reactive ion etching (DRIE), which is a highly anisotropic etching scheme that can combine both physical milling and chemical etching. In some embodiments, the one or more implant CMOS integrated circuits 106 are separated using trenches 501.

Figure 5F:
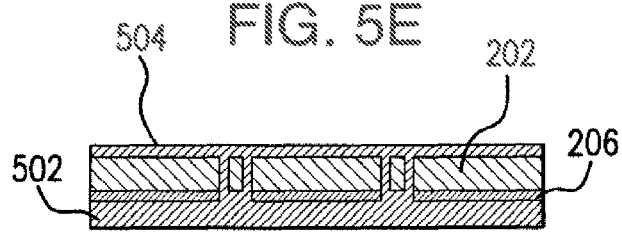
Figure 5G:
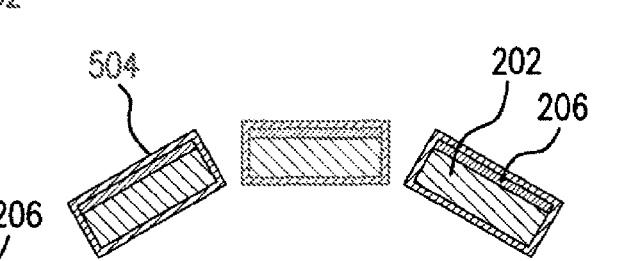

FIG. 5F shows backside encapsulation using an additional biocompatible layer 504 and performed similarly to the encapsulation illustrated in FIG. 5C. Lastly, the one or more implant CMOS integrated circuits 106 are released from a handle wafer by, for example, scooping them out or by centrifugation or any other suitable release mechanism. In some embodiments, the one or more implant CMOS integrated circuits 106 are collected in de-ionized water.

Figure 6:
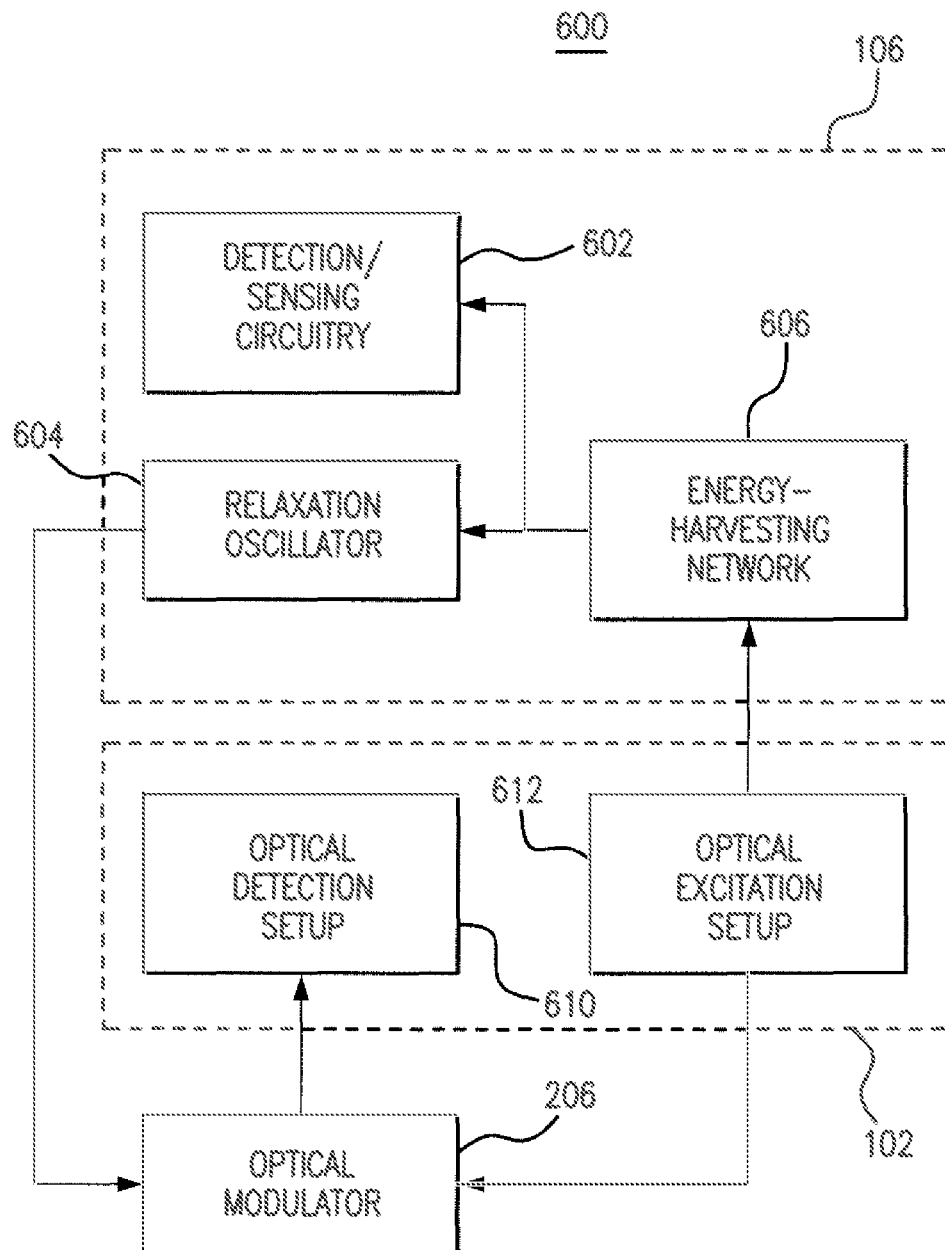
FIG. 6 illustrates an exemplary block diagram of a system for performing non-destructive sensing and imaging of a cell, in accordance with one or more embodiments.

In some embodiments and as discussed above, implant IC chip 106 can include additional sensing and processing circuitry and data transfer circuitry integrated within using one or more of the fabrication processes illustrated in FIGS. 3A-5G. FIG. 6 illustrates an exemplary block diagram of a system for performing non-destructive sensing and imaging of a cell. In some embodiments, the implant IC chip 106 can be illuminated from a light source included in microscope 102 and the optically modulated data signal by the optical modulator 206 can also be captured by the microscope 102.

Specifically, implant IC chip 106 can be injected into a cell and placed on microscopic slide 104 under microscope 102.

Subsequently, implant IC chip 106 is exposed to a light source included into the optical excitation setup module 612 of microscope 102. In some embodiments, the light source can be a lamp, flash light, LED light or any other suitable light source integrated in microscope 102. Upon exposure to the light source, the energy harvesting network 208 of implant IC chip 106 collects the illuminated energy. In some embodiments, energy harvesting network can include one or more photovoltaic cells 208 that can generate a DC voltage capable of powering the implant IC chip 106 including the relaxation oscillator 604 and any additional detection/sensing circuitry 602.

In some embodiments detection/sensing circuitry 602 can include electrophysiological probes, or any other suitable circuitry capable of detecting and obtaining a measurement signal relating to, for example, intracellular activity. The detected signal is subsequently modulated through optical modulator 206. Specifically, the spectrum of the excitation light, illuminated by optical excitation setup module 612 of microscope 102, can be separated for powering both the implant IC chip 106 using energy harvesting circuitry 208 and for data transmission using optical modulator 206. As a result, the implant IC chip 106 can allow for simultaneous observation and powering under microscope 102. In addition, relaxation oscillator 604 is powered by energy harvesting circuitry 208 and can drive optical modulator 206 by adjusting the oscillation frequency of the transmitted optical signal.

Figure 7A:
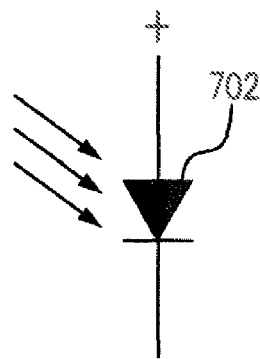
FIGS. 7A-7D illustrate exemplary circuit diagrams of energy harvesting circuitry of the disclosed integrated circuit, in accordance with one or more embodiments.
Figure 7C:
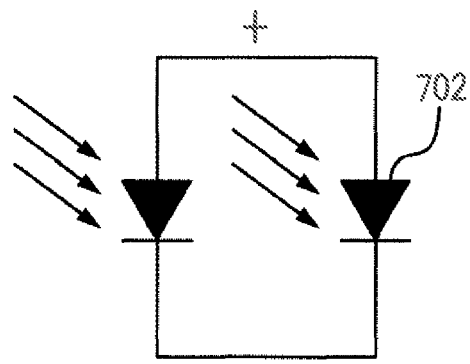
Figure 7B:
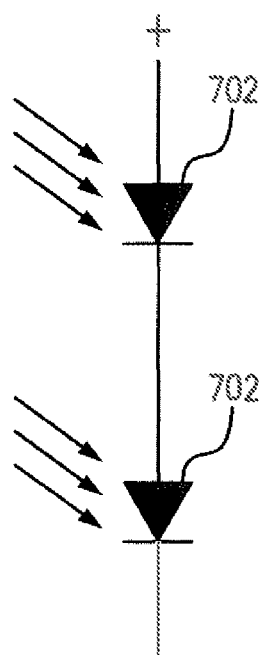

FIGS. 7A-7D illustrate exemplary circuit diagrams of energy harvesting circuitry 208 integrated in implant IC chip 106. In some embodiments, energy harvesting circuitry 208 can be integrated on-chip and include one or more photovoltaic cells capable of powering IC chip 106, as shown in reference to FIG. 2B. Specifically, in some embodiments, the photovoltaic cells can be constructed using a network of diodes connected in different configurations. For example, FIG. 7A illustrates a photovoltaic cell constructed using a single photodiode 702. FIG. 7B illustrates two photodiodes 702 connected in series that are capable of providing a higher voltage supply to implant IC chip 106.

Figure 7D:
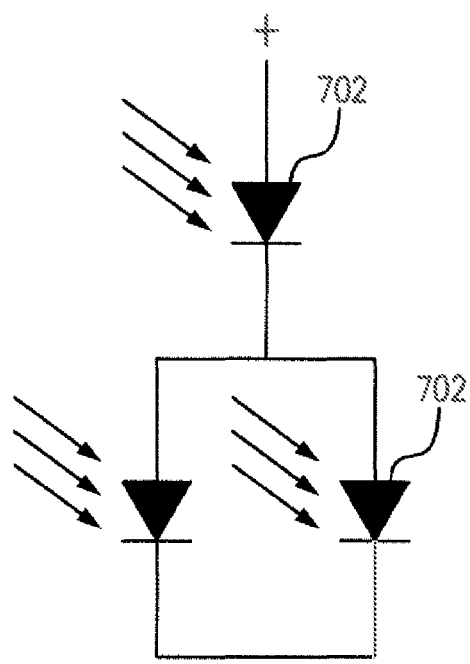

FIG. 7C illustrates two photodiodes 702 connected in parallel that are capable of providing a lower output impedance when powering implant IC chip 106. Additionally, FIG. 7D illustrates a photodiode 702 connected in series to two photodiodes 702 connected in parallel. In some embodiments, any number and combination of photodiodes 702 and/or isolated SOI diodes can be used for constructing the photovoltaic cells of energy harvesting circuitry 208.

The photodiodes 702, previously discussed in reference to FIGS. 7A-D can be fabricated using available p-n junctions in the CMOS process, as shown in FIGS. 8A-8E. In some embodiments, photodiodes 702 can include substrate-well diodes, diffusion-well diodes, substrate-diffusion diodes, triple-well diodes, polysilicon diodes, isolated diode junctions available in an SOI process, or any other suitable diode.

FIG. 8A illustrates an exemplary photodiode 702 that can be used as photovoltaic cells in a CMOS process frontend according to the disclosed subject matter. Specifically, FIG. 8A shows a p-diffusion n-well diode fabricated using a p-type substrate. FIG. 8B shows an n-diffusion p-well diode fabricated using a deep n-type substrate. FIG. 8C shows a p-well deep n-well diode. FIG. 8D shows a p-diffusion n-well diode on an SOI substrate and FIG. 8E shows n-diffusion p-well diode on an SOI substrate. In some embodiments, SOI isolated diodes can be utilized at least because of the absence of a leaky parasitic substrate diode.

Figure 9:
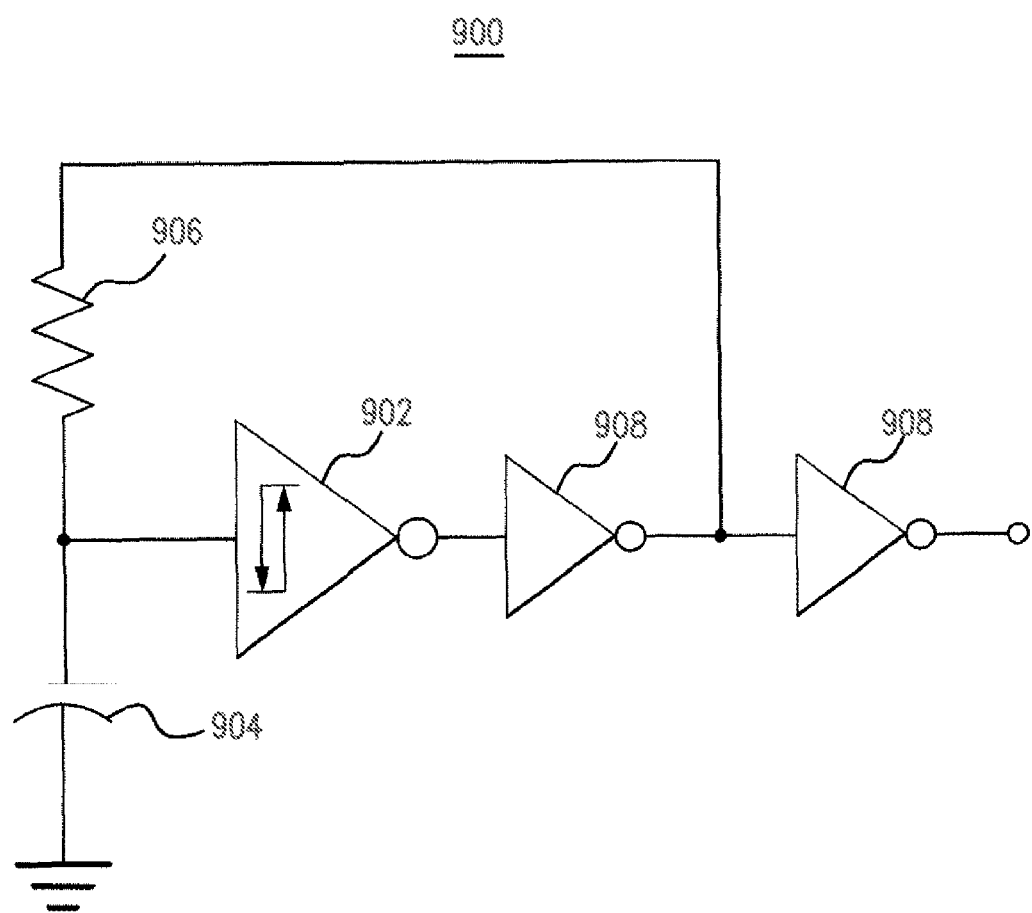
FIG. 9 illustrates an exemplary circuit diagram of a relaxation oscillator of the disclosed integrated circuit, in accordance with one or more embodiments.
Figure 10:
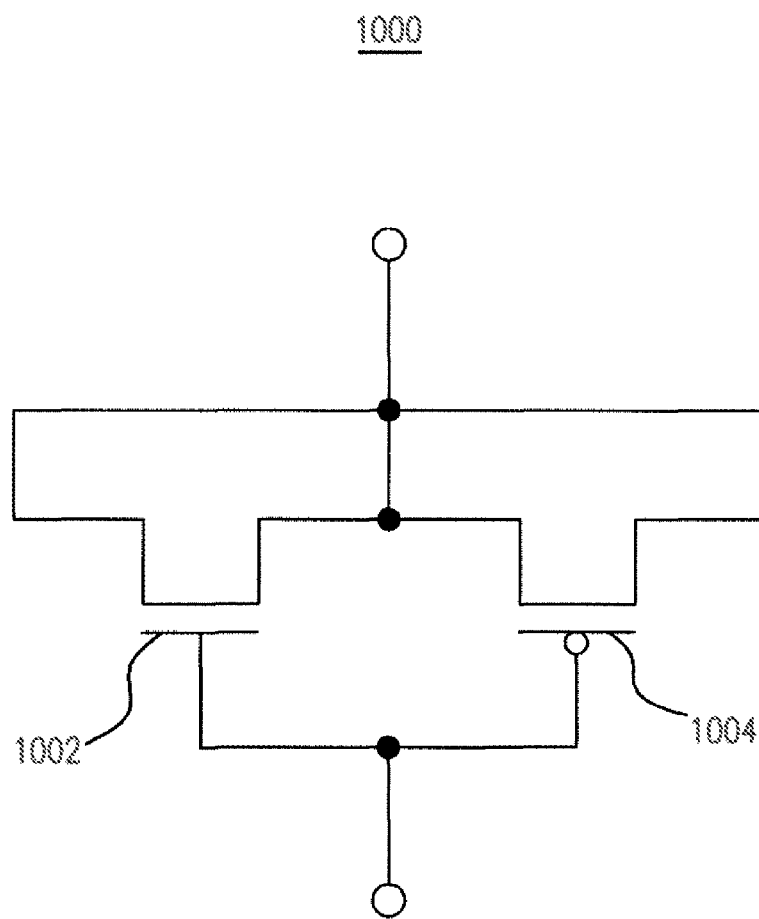
FIG. 10 illustrates an exemplary circuit diagram of the gate leakage resistance of FIG. 9, in accordance with one or more embodiments.

FIG. 9 illustrates an exemplary circuit diagram of relaxation oscillator 604 including comparator 902 logic NOT gates 908, resistor 906 and capacitor 904 forming a positive feedback loop that allows for the circuit too oscillate automatically. The low-power relaxation oscillator 604 can be used to drive the optical modulator 208 by adjusting and setting an oscillation frequency. For example, as shown in FIG. 10, a gate-leakage resistor 1000 can be used to implement the leakage current that defines oscillation frequency. The gate-leakage resistor 1000 includes a p-channel MOSFET transistor 1004 connected to an N-channel MOSFET transistor 1002 that can achieve a large time constant using a small area constraint and provide a symmetric rise and fall time for the relaxation oscillator 604 and a duty cycle close to 50%. In some embodiments, the long time constant and low oscillation frequency can allow the usage of a reasonably long exposure time to image the implant IC chip 106.

Figure 11:
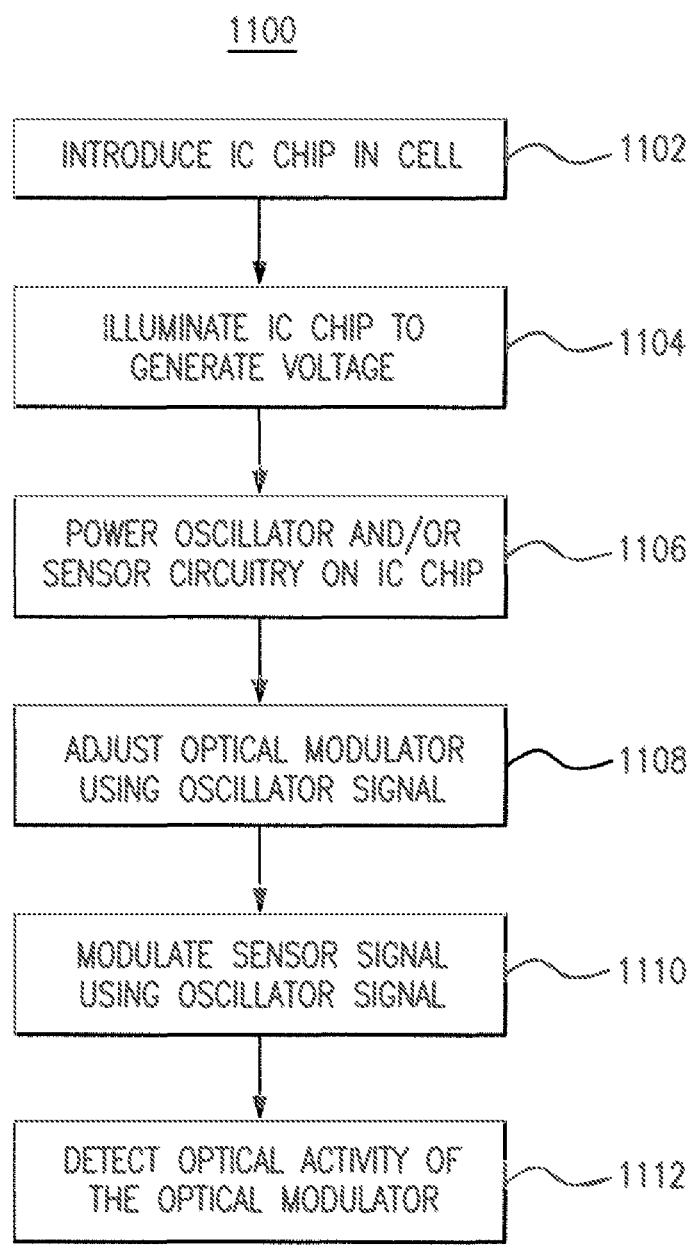
FIG. 11 illustrates an exemplary process flow chart for performing non-destructive sensing and imaging of a cell, in accordance with one or more embodiments.

FIG. 11 illustrates an exemplary process flow chart for performing non-destructive sensing and imaging of a cell. Specifically, at 1202 implant IC chip 106 is introduced to a tissue of interest e.g., a cell. In some embodiments, one or more implant IC chips 106 can be introduced to different cells by injection/microinjection and/or tosis. At 1204 implant IC chip 106 is illuminated by a light source in order to harvest energy using energy harvesting circuitry 208 and produce DC voltage. In some embodiments, the light source can be integrated into microscope 102. The produced DC voltage subsequently powers optical oscillator 206 and detection/sensing circuitry 602 at 1106. At 1108, the measured signal by detection/sensing circuitry 602 is modulated by optical modulator 208 in order to transmit an optical signal. At 1110, the relaxation oscillator can adjust the oscillation frequency for optical modulator 208 and at 1112 the modulated optical signal is detected by an image sensor. In some embodiments, the image sensor can be integrated into microscope 102.

Unless specifically stated otherwise, as apparent from the following discussions, it is appreciated that throughout the specification discussions utilizing terms such as "processing," "computing," "determining," or the like, refer to the action and/or processes of a computer or computing system, or similar electronic computing device, that manipulates and/or transforms data represented as physical, such as electronic, quantities within the computing system's registers and/or memories into other data similarly represented as physical quantities within the computing system's memories, registers or other such information storage, transmission or display devices.

Although one or more embodiments have been described herein in some detail for clarity of understanding, it should be recognized that certain changes and modifications can be made without departing from the spirit of the disclosure. Features of certain embodiments can be combined with features of other embodiments; thus certain embodiments can be combinations of features of multiple embodiments. The embodiments described herein can employ various computer-implemented operations involving data stored in computer systems. For example, these operations can require physical manipulation of physical quantities—usually, though not necessarily, these quantities can take the form of electrical or magnetic signals, where they or representations of them are capable of being stored, transferred, combined, compared, or otherwise manipulated. Further, such manipulations are often referred to in terms, such as producing, yielding, identifying, determining, or comparing.

Any operations described herein that form part of one or more embodiments of the disclosure can be useful machine operations. In addition, one or more embodiments of the disclosure also relate to a device or an apparatus for performing these operations. The apparatus can be specially constructed for specific required purposes, or it can be a general purpose computer selectively activated or configured by a computer program stored in the computer. In particular, various general purpose machines can be used with computer programs written in accordance with the teachings herein, or it can be more convenient to construct a more specialized apparatus to perform the required operations.

In the claims, elements do not imply any particular order of operation, unless explicitly stated in the claims. In general, structures and functionality presented as separate components in exemplary configurations can be implemented as a combined structure or component. Similarly, structures and functionality presented as a single component can be implemented as separate components. These and other variations, modifications, additions, and improvements can fall within the scope of the appended claim(s).

What is claimed is:

1. A system for performing non-destructive sensing of one or more cells or tissues, the system comprising:
    an integrated circuit, comprising:
    an energy harvestor configured to collect energy from an optical source;
    a sensor, coupled to the energy harvestor to be powered thereby, and configured to measure one or more signals associated with the one or more cells or tissues; and
    at least one electro-optical modulator comprising a plurality of fluorescent materials, coupled to the sensor and configured to modulate the one or more signals as one or more optical signals.

2. The system of claim 1, wherein the one or more measured signals are electrochemical signals.

3. The system of claim 1, wherein the energy harvestor comprises one or more photovoltaic cells.

4. The system of claim 3, wherein the one or more photovoltaic cells are comprised of one or more diodes.

5. The system of claim 1, wherein the one or more cells or tissues are sensed in vivo.

6. The system of claim 1, wherein the one or more measured signals are electrical signals.

7. The system of claim 1, wherein the integrated circuit is fabricated to have a thickness of 10 μm.

8. The system of claim 1, further comprising an imaging sensor configured to detect and display the one or more optical signals.

9. The system of claim 1, wherein the imaging sensor is selected from a group consisting of a CCD image sensor, a CMOS image sensor, a spectrometer and an image sensor mounted on a microscope.

10. The system of claim 1, wherein the integrated circuit is implanted in the one or more cells or tissues by injection.

11. The system of claim 1, wherein the integrated circuit is implanted in the one or more cells or tissues by micro-injection.

12. The system of claim 1, wherein the integrated circuit is introduced in the one or more cells or tissues by use of a micropipette from a dispersion or solution in a compatible solvent such as deionized water.

13. The system of claim 1, wherein the integrated circuit is implanted in the one or more cells by endocytosis.

14. The system of claim 1, wherein the plurality of fluorescent materials form a capacitor comprising a layer of quantum dots.

15. The system of claim 1, wherein the integrated circuit further comprises a relaxation oscillator coupled to the at least one optical modulator.

16. The system of claim 1, wherein the one or more cells or tissues are sensed in culture.

* * * * *